(12) United States Patent
Stanton, Jr.

(10) Patent No.: US 6,379,896 B1
(45) Date of Patent: *Apr. 30, 2002

(54) PROBES FOR VARIANCE DETECTION

(75) Inventor: Vincent P. Stanton, Jr., Belmont, MA (US)

(73) Assignee: Variagenics, Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/697,097

(22) Filed: Oct. 26, 2000

Related U.S. Application Data

(62) Division of application No. 09/073,717, filed on May 6, 1998, now Pat. No. 6,183,958.

(51) Int. Cl.⁷ .......................... C12Q 1/68; C12P 19/34; C07H 21/02; C07H 21/04; C12N 1/20

(52) U.S. Cl. .................. 435/6; 435/69.1; 435/91.2; 435/252.3; 536/23.1; 536/24.1; 536/24.3; 536/24.31; 536/24.33

(58) Field of Search ................. 435/6, 91.2, 252.3; 536/24.1, 24.3, 24.31, 24.33

(56) References Cited

U.S. PATENT DOCUMENTS

| | | | |
|---|---|---|---|
| 5,422,253 A | * 6/1995 | Dahlberg et al. | 435/91.53 |
| 5,698,400 A | 12/1997 | Cotton et al. | 435/6 |
| 5,707,809 A | * 1/1998 | Halverson | 435/6 |
| 5,962,223 A | * 10/1999 | Whiteley | 435/6 |
| 6,180,776 B1 | * 1/2001 | Kamb | 536/24.1 |
| 6,183,958 B1 | * 2/2001 | Stanton | 435/6 |

OTHER PUBLICATIONS

Abrams, E.S. et al., "Comprehensive Detection of Single Base Changes in Human Genomic DNA Using Denaturing Gradient Gel Electrophoresis and a GC Clamp," Genomics 7: 463–475, 1990.

Abrams and Stanton Jr., "Use of Denaturing Gradient Gel Electrphoresis to Study Conformational Transitions in Nucleic Acids," Methods in Enzymology 212: 71–104, 1992.

Casas and Kirkpatrick, "Evaluation of Different Amplification Protocols for Use in Primer–Extension Preamplification," BioTechniques 20: 219–225, 1996.

Cotton et al., "Reactivity of Cytosine and Thymine in Single–Base–Pair Mismatches with Hydroxylamine and Osmium Tetroxide and Its Application to the Study of Mutations," Proc. Natl. Acad. Sci. USA 85: 4397–4401, 1988.

Cotton, R.G.H., "Current Methods of Mutation Detection," Mutation Research 285: 125–144, 1993.

Cotton and Campbell, "Chemical Reactivity of Matched Cytosime and Thymine Bases Near Mismatched and Unmatched Bases in a Heteroduplex Between DNA Strands with Multiple Differences," Nucleic Acids Research 17: 4223–4233, 1989.

Cui et al., "Gene–centromere Linkage Mapping by PCR Analysis of Individual Oocytes," Genomics 13: 713–717, 1992.

Debbie, P. et al., "Allele Identification Using Immobilized Mismatch Binding Protein: Detection and Identification of Antibiotic–Resistant Bacteria and Determination of Sheep Susceptibility to Scrapie," Nucleic Acids Research 25: 4825–4829, 1997.

Fischer and Lerman, "DNA Fragments Dffering by Single Base–Pair Substitutions are Separated in Denaturing Gradient Gels: Correspondence with Melting Theory," Proc. Natl. Acad. Sci. USA 80: 1579–1583, 1983.

Fischer and Lerman, "Two–Dimensional Electrophoretic Separation of Restriction Enzyme Fragments of DNA," Methods in Enzymology 68: 183–191, 1979.

Ganguly et al., "Conformation–Sensitive Gel Electrophoresis for Rapid Detection of Single–Base Differences in Double–Stranded PCR Products and DNA Fragments: Evidence for Solvent–Induced Bends in DNA Heteroduplexes," Proc. Natl. Acad. Sci. USA 90: 10325–10329, 1993.

Goldrick et al., "NIRCA™: A Rapid Robust Method for Screening for Unknown Point Mutations," BioTechniques 21: 106–112, 1996.

Li et al., "Direct Electrophoretic Detection of the Allelic State of Single DNA Molecules in Human Sperm by Using the Polymerase Chain Reaction," Proc. Natl. Acad. Sci. USA 87: 4580–4584, 1990.

Mashal et al., "Detection of Mutations by Cleavage of DNA Heteroduplexes with Bacteriophage Resolvases," Nature Genetics 9: 177–183, 1995.

Michalatos–Beloin et al., "Molecular Haplotyping of Genetic Markers 10 kb Apart by Allele–Specific Long–Range PCR," Nucleic Acids Research 24: 4841–4843, 1996.

Myers et al.,"Mutation Detection by PCR, GC–Clamps, and Denaturing Gradient Gel Electrophoresis," pp. 71–88 in Erlich, H.A. (ed.), *PCR Technology: Principles and Applications for DNA Amplification*, Stockton Press, New York, 1989.

Myers et al., "Detecting Changes in DNA: Ribonuclease Cleavage and Denaturing Gradient Gel Electrophoresis," pp. 95–139 in Davies, K.E. (ed.), *Genomic Analysis: A Practical Approach*, IRL Press Ltd., Oxford, 1988.

Myers et al., "Detection of Single Base Substitutions by Ribonuclease Cleavage at Mismatches in RNA:DNA Duplexes," Science 230: 1242–1246, 1985.

Myers et al., "Nearly All Single Base Substitutions in DNA Fragments Joined to a GC–clamp Can Be Detected By Denaturing Gradient Gel Electrophoresis," Nucleic Acids Research 13: 3131–3145, 1985.

(List continued on next page.)

*Primary Examiner*—Jeffrey Fredman
*Assistant Examiner*—Arun Kr. Chakrabarti
(74) *Attorney, Agent, or Firm*—Clark & Elbing, LLP

(57) ABSTRACT

Disclosed are methods and reagents for detecting nucleotide mismatches (for example, due to sequence variances) in a nucleic acid sample involving the use of a nucleic acid probe derived from a hemizygous cell. Methods for determining the haplotype of a nucleic acid sample are also disclosed. Also disclosed are methods for producing the probe and kits containing the probe.

39 Claims, 1 Drawing Sheet

OTHER PUBLICATIONS

Novack et al., "Detection of Single Base–Pair Mismatches in DNA by Chemical Modification Followed by Electrophoresis in 15% Polyacrylamide Gel," Proc. Natl. Acad. Sci. USA 83: 586–590, 1986.

Orita et al., "Rapid and Sensitive Detection of Point Mutations and DNA Polymorphisms Using the Polymerase Chain Reaction," Genomics 5: 874–879, 1989.

Roberts et al., "Potassium Permanganate and Tetraethylammonium Chloride are a Safe and Effective Substitute for Osmium Tetroxide in Solid–Phase Fluorescent Chemical Cleavage of Mismatch," Nucleic Acids Research 25: 3377–3378, 1997.

Smooker et al., "Identification and In Vitro Expression of Mutations Causing Dihydropteridine Reductase Deficiency," Biochemistry 32: 6443–6449, 1993.

Smooker and Cotton, "The Use of Chemical Reagents in the Detection of DNA Mutations," Mutation Research 288: 65–77, 1993.

Snabes et al., "Preimplantation Single–Cell Analysis of Multiple Genetic Loci by Whole–Genome Amplification," Proc. Natl. Acad. Sci. USA 91: 6181–6185, 1994.

Wagner, R. et al., "Mutation Detection Using Immobilized Mismatch Binding Protein (MutS)," Nucleic Acids Research 23: 3944–3948, 1995.

White et al., "Detecting Single Base Substitutions as Heteroduplex Polymorphisms," Genomics 12: 301–306, 1992.

Williams et al., "Three New Point Mutations in Type II Procollagen (COL2A1) and Identification of a Fourth Family With the COL2A1 Arg519→Cys Base Substitution Using Conformation Sensitive Gel Electrophoresis," Hum. Mol. Gen. 4: 309–312, 1995.

Youil et al., "Detection of 81 of 81 Known Mouse β–Globin Promoter Mutations with T4 Endonuclease VII–The EMC Method," Genomics 32: 431–435, 1996.

Youil et al., "Screening for Mutations by Enzyme Mismatch Cleavage with T4 Endonuclease VII," Proc. Natl. Acad. Sci. USA 92: 87–91, 1995.

Zhang et al., "Whole Genome Amplification From a Single Cell: Implications for Genetic Analysis," Proc. Natl. Acad. Sci. USA 89: 5847–5851, 1992.

Litt et al., "Rapid RFLP Screening Using DNA From Complete Hydatidiform Moles," *Nucleic Acids Res.* 17(1):464 (1989).

Taillon–Miller et al., "The Homozygous Complete Hydatidiform Mole: A Unique Resource For Genome Studies," *Genomics* 46(2):307–310 (1997).

* cited by examiner

|         | Variance #1 | Variance #2 |
|---------|-------------|-------------|
| 1       | A / T       | C / G       |
| 2       | A / T       | G / C       |
| 3       | G / C       | C / G       |
| 4       | G / C       | G / C       |

PROBES FOR VARIANCE DETECTION

This application is a divisional of U.S. patent application Ser. No. 09/073,717, filed May 6, 1998, now U.S. Pat. No. 6,183,958.

BACKGROUND OF THE INVENTION

This invention relates to methods and reagents for detecting mispaired nucleotides in duplex nucleic acids for use, for example, in identifying genetic variations in nucleic acid sequences for research, therapeutic, and diagnostic applications.

Genetic variation occurs at approximately 1 out of every 100 bases within the genome. Research aimed at discovering genetic variation associated with diseases or disease therapies, as well as diagnostic tests aimed at using genetic information to manage patient care, requires efficient methods for detecting and typing genetic variance in various test sequences. Variances may be detected by a variety of methods. Many of these methods require the use of a probe with a unique sequence (representing a single allelic form of the sequence) as a reference by which to identify differences in the sequences of homologous DNA segments in patient test samples. Probes with a unique sequence are commonly produced from cloned DNA or cDNA. However, the use of probes from cloned DNA limits the ability to identify variances to DNA segments for which such clones are readily available, or alternatively requires the cloning of each DNA segment to be analyzed.

SUMMARY OF THE INVENTION

The present invention involves a general method for obtaining and using probes with unique sequences (monoallelic probes) from certain cells or tissues that are hemizygous for genes, chromosomal segments, or chromosomes that are the object of the analysis. Such probes are useful for the analysis of sequence variation, for example, by heteroduplex formation.

Accordingly, in a first aspect, the invention features a method for detecting a nucleotide mismatch in a nucleic acid sample that includes the steps of: (a) providing a nucleic acid probe derived from a hemizygous cell, the probe being complementary to a hemizygous chromosome or segment thereof present in the hemizygous cell; (b) forming a duplex between the nucleic acid sample and the probe; and (c) determining if the duplex contains a nucleotide mismatch.

In various embodiments of this aspect of the invention, the determining step is carried out using a denaturing gradient gel electrophoresis technique; the nucleotide mismatch represents a sequence variance in a population; the probe has a known sequence, and may be detectably labeled; the hemizygous cell results from the loss of a chromosome or segment thereof; the hemizygous cell includes multiple copies of the hemizygous chromosome or segment thereof; the hemizygous cell may be human; the hemizygous cell may be an immortalized cell; the hemizygous cell may be derived from a complete hydatidiform mole, an ovarian teratoma, an acute lymphocytic leukemia, an acute myeloid leukemia, a solid tumor, a squamous cell lung cancer, an endometrial ovarian cancer, a malignant fibrous histiocytoma, or a renal oncocytoma; the hemizygous cell may be NALM-16 or KBM-7; and the hemizygous cell may be derived from a haploid germ cell.

In yet other embodiments of the first aspect of the invention, the presence of the nucleotide mismatch correlates with a level of therapeutic responsiveness to a drug or other therapeutic intervention; the presence of the nucleotide mismatch indicates a disease or condition, or a predisposition to develop the disease or condition; the nucleic acid probe is produced by amplifying at least a portion of the hemizygous chromosome or segment thereof to produce the probe; the determining step utilizes a protein that binds or cleaves the nucleotide mismatch, for example, MutS or a resolvase (e.g., T4 endonuclease VII), and the determining step utilizes a chemical agent that detects the nucleotide mismatch. This method of the first aspect of the invention may be used to determine the haplotype of the nucleic acid sample.

In a second aspect, the invention features a method for detecting a nucleotide mismatch in a nucleic acid sample that includes the steps of: (a) providing a nucleic acid probe derived from a sex chromosome; (b) forming a duplex between the nucleic acid sample and the probe; and (c) determining if the duplex contains a nucleotide mismatch.

In a third aspect, the invention features a method for detecting a nucleotide mismatch in a nucleic acid sample that includes the steps of: (a) providing a nucleic acid probe derived from a somatic cell hybrid, the probe being complementary to a chromosome or segment thereof, where only one allele of the chromosome or segment thereof is present in the somatic cell hybrid; (b) forming a duplex between the nucleic acid sample and the probe; and (c) determining if the duplex contains a nucleotide mismatch.

In a fourth aspect, the invention features a kit for detecting a nucleotide mismatch that includes: (a) a nucleic acid probe derived from a hemizygous cell, the probe being complementary to a hemizygous chromosome or segment thereof; and (b) a means for detecting a nucleotide mismatch. In preferred embodiments, the probe is detectably labeled; the detecting means is a protein that binds or cleaves the nucleotide mismatch, for example, MutS or a resolvase (e.g., T4 endonuclease VII); and the detecting means is a chemical agent that detects the nucleotide mismatch.

In a fifth aspect, the invention features a method for producing a nucleic acid probe for the detection of a nucleotide mismatch that includes the steps of: (a) providing a hemizygous cell having at least one hemizygous chromosome or segment thereof; and (b) amplifying at least a portion of the hemizygous chromosome or segment thereof to produce the probe.

In a sixth aspect, the invention features a method for producing a nucleic acid probe for the detection of a nucleotide mismatch that includes the steps of: (a) providing nucleic acid from a hemizygous cell having at least one hemizygous chromosome or segment thereof; and (b) using the nucleic acid to produce a probe, the probe being complementary to at least a portion of the hemizygous chromosome or segment thereof. In one preferred embodiment, the nucleic acid is amplified, where the amplified nucleic acid is a representation of the genomic DNA of the hemizygous cell. In another embodiment of this aspect, the nucleic acid is an RNA or DNA library.

In preferred embodiments of the fifth and sixth aspects of the invention, the probe has a known sequence; the method further includes detectably labeling the probe; the hemizygous cell may be human; the hemizygous cell may be an immortalized cell; the hemizygous cell may be derived from a complete hydatidiform mole, an ovarian teratoma, an acute lymphocytic leukemia, an acute myeloid leukemia, a solid tumor, a squamous cell lung cancer, an endometrial ovarian cancer, a malignant fibrous histiocytoma, or a renal oncocytoma; the hemizygous cell is NALM-16 or KBM-7; and the hemizygous cell may be derived from a haploid germ cell.

In a seventh aspect, the invention features a nucleic acid probe for the detection of a nucleotide mismatch, the probe being derived from a hemizygous cell and being complementary to a hemizygous chromosome or segment thereof. In a preferred embodiment of this aspect of the invention, the probe is detectably labeled.

In an eighth aspect, the invention features a nucleic acid probe derived from an autosomal chromosome of a mammalian cell, the probe having a unique sequence. In one preferred embodiment of this aspect of the invention, the probe is detectably labeled In a final aspect, the invention features a method for determining if two nucleotide mismatches are located on the same strand of DNA in a nucleic acid sample that includes the steps of: (a) providing a first nucleic acid probe derived from a hemizygous cell, the first nucleic acid probe having a first unique sequence; (b) forming a first duplex between the nucleic acid sample and the first nucleic acid probe; (c) contacting the first duplex with a compound that cleaves a duplex containing a nucleotide mismatch under conditions which allow the compound to cleave the first duplex if the first duplex contains a nucleotide mismatch; (d) providing a second nucleic acid probe derived from a hemizygous cell, the second nucleic acid probe having a second unique sequence; (e) forming a second duplex between the product of step (c) and the second nucleic acid probe; (f) contacting the second duplex with the compound under conditions which allow the compound to cleave the second duplex if the second duplex contains a nucleotide mismatch; and (g) comparing the product of step (c) with the product of step (f), a reduction in the size of the product of step (f) compared to the product of step (c) indicating that both the nucleotide mismatches are located on the same strand of DNA in the nucleic acid sample.

In preferred embodiments of the ninth aspect of the invention, the method is used to determine the haplotype of the nucleic acid sample; and three or more nucleic acid probes are provided, each derived from a hemizygous cell and having a different unique sequence, and, for each nucleic acid probe, steps (e)—(g) are repeated, and the products of each cleavage step compared.

In other embodiments of this aspect of the invention, the compound may be a resolvase (e.g., T4 endonuclease VII) or may be a chemical; the comparing step is carried out using a denaturing gradient gel electrophoresis technique; the first nucleic acid probe and the second nucleic acid probe are derived from the same hemizygous cell; the first and second nucleic acid probes may have a known sequence, and may be detectably labeled; the hemizygous cell results from the loss of a chromosome or segment thereof; the hemizygous cell includes multiple copies of the hemizygous chromosome or segment thereof; the hemizygous cell may be human; the hemizygous cell may be an immortalized cell; the hemizygous cell may be derived from a complete hydatidiform mole, an ovarian teratoma, an acute lymphocytic leukemia, an acute myeloid leukemia, a solid tumor, a squamous cell lung cancer, an endometrial ovarian cancer, a malignant fibrous histiocytoma, or a renal oncocytoma; the hemizygous cell may be NALM-16 or KBM-7; and the hemizygous cell may be derived from a haploid germ cell.

In yet other embodiments of the ninth aspect of the invention, the location of two nucleotide mismatches on the same strand of DNA in a nucleic acid sample correlates with a level of therapeutic responsiveness to a drug or other therapeutic intervention; the location of two nucleotide mismatches on the same strand of DNA in a nucleic acid sample indicates a disease or condition, or a predisposition to develop the disease or condition; and the nucleic acid probes are produced by amplifying at least a portion of the hemizygous chromosome or segment thereof to produce the probes.

By a "hemizygous cell" is meant a mammalian cell having one or more autosomal chromosomes, or segments thereof, which are derived from only one parental copy and whose genome therefore contains one unique sequence (i.e., is completely homozygous) at those chromosomal locations. Included within this definition is a cell having two (or even more) identical copies of this unique sequence chromosome (or segment thereof), most commonly as the result of a chromosomal duplication event. Such unique sequence autosomal chromosomes are referred to herein as "hemizygous chromosomes."

By a "unique sequence" is meant the nucleotide sequence of the hemizygous chromosomes in a hemizygous cell, where substantially all of the homologous chromosomes in the cell contain the same base at every position within the sequence. By a probe having a "unique sequence" is meant that substantially all copies of the probe made from a hemizygous cell contain the same base at every position within the sequence. In a solution of such a unique sequence probe, different bases comprise less than 1%, preferably, less than 0.1%, and, more preferably, less than 0.01% of the bases present at any given position in that probe in the solution. Typically, these low frequency base changes are introduced during probe preparation (for example, during PCR amplification) and do not represent base differences present in the chromosomal sequence from which the probe was generated. By "base" is meant a nucleotide, including an A (dATP), G (dGTP), C (dCTP), or T (dTTP) for DNA, and an A (ATP), G (GTP), C (CTP), or U (UTP) for RNA, as well as chemical derivatives of these bases commonly known in the art that are substrates for polymerases and which may be incorporated into amplified sequences.

By a "probe" is meant a nucleic acid molecule derived from a gene, chromosomal segment, or chromosome that is used as a reference, for example, in variance detection to determine whether a test sample of the same gene, chromosomal segment, or chromosome derived from a particular individual contains the identical sequence or a different sequence at one or more nucleotide positions. Probes may be derived from genomic DNA or cDNA, for example, by amplification, or from cloned DNA segments and, most commonly, contain either genomic DNA or cDNA sequences representing all or a portion of a single gene from a single individual. Preferably, the probe has a unique sequence (as defined above) and/or has a known sequence.

By "autosomal chromosome" is meant any chromosome within a normal somatic or germ cell except the sex chromosomes. In humans, for example, chromosomes 1–22 are autosomal chromosomes.

By "sex chromosome" is meant a chromosome, or a segment thereof, the presence, absence, or alteration of which affects the gender of the organism from which the chromosome is derived. Human sex chromosomes, for example, are the X chromosome and the Y chromosome.

By a "haploid germ cell" is meant a sperm cell or an oocyte (i.e., an unfertilized egg cell).

By "haplotype" is meant an allele or a group of alleles (i.e., a specific set of nucleotides at variant positions) on a single chromosome or segment thereof.

By "polypeptide" or "protein" is meant any chain of amino acids, regardless of length or post-translational modification (for example, glycosylation or phosphorylation).

By "detectably labeled" is meant that a molecule is marked or identified by some means that may be observed or assayed. Methods for detectably labeling a molecule are well known in the art and include, without limitation, radioactive labeling (for example, with an isotope such as $^{32}$P or $^{35}$S), enzymatic labelling (for example, using horseradish peroxidase), chemiluminescent labeling, and fluorescent labeling (for example, using fluorescein). Also included in this definition is a molecule that is detectably labeled by an indirect means, for example, a molecule that is bound with a first moiety (such as biotin) that is, in turn, bound to a second moiety that may be observed or assayed (such as fluorescein-labeled streptavidin).

By "resolvase" is meant any protein that is capable of cleaving a mismatch (for example, a mismatch loop) in a heteroduplex, or is capable of cleaving a cruciform DNA. Examples of resolvases include, without limitation, T4 endonuclease VII, Saccharomyces cerevisiae Endo X1, Endo X2, Endo X3, and CCE1 (Jensch et al., EMBO J. 8: 4325–4334, 1989; Kupfer and Kemper, Eur. J. Biochem. 238: 77–87, 1996), T7 endonuclease I, E. coli MutY (Wu et al., Proc. Natl. Acad. Sci. USA 89: 8779–8783, 1992), mammalian thymine glycosylase (Wiebauer et al., Proc. Natl. Acad. Sci. USA 87: 5842–5845, 1990), topoisomerase I from human thymus (Yeh et al., J. Biol. Chem. 266: 6480–6484, 1991; Yeh et al., J. Biol. Chem. 269: 15498–15504, 1994), and deoxyinosine 3' endonuclease (Yao and Kow, J. Biol. Chem. 269: 31390–31396, 1994). To carry out mismatch detection, one or several resolvases may be utilized. A resolvase represents one type of protein that may be used to detect a mismatch.

By "bindase" is meant any protein that is capable of specifically binding to, but not cleaving, a heteroduplex. A bindase represents one type of protein that may be used to detect a mismatch, and may be used alone, with another bindase, or with one more resolvases to carry out mismatch detection. One exemplary bindase is E. coli MutS.

By a "chemical agent that detects a heteroduplex" is meant a chemical agent that modifies mismatched nucleotides. Examples of such chemical agents are carbodiimide, hydroxylamine, osmium tetroxide, and potassium permanganate which are used in the carbodiumide (CDI) and the Chemical Cleavage of Mismatch (CCM) methods (Smooker and Cotton, Mutat. Res. 288: 65–77, 1993; Roberts et al., Nucl. Acids Res. 25:3377–3378, 1997). In a given mismatch detection assay, one or several chemical agents or methods may be utilized.

By "duplex" is meant a structure formed between two annealed complementary nucleic acid strands (for example, one nucleic acid strand from a test sample and one nucleic acid strand from a probe) in which sufficient sequence complementarity exists between the strands to maintain a stable hybridization complex. A duplex may be either a homoduplex, in which all of the nucleotides in the first strand appropriately base pair with all of the nucleotides in the second opposing complementary strand, or a heteroduplex. By a "heteroduplex" is meant a structure formed between two annealed strands of nucleic acid in which one or more nucleotides in the first strand do not or cannot appropriately base pair with one or more nucleotides in the second opposing (i.e., complementary) strand because of one or more mismatches. Examples of different types of heteroduplexes include those which exhibit an exchange of one or several nucleotides, and insertion or deletion mutations, each of which is described in Bhattacharyya and Lilley (Nucl. Acids Res. 17: 6821–6840, 1989).

By "complementary" is meant that two nucleic acids, e.g., DNA or RNA, contain a sufficient number of nucleotides which are capable of forming Watson-Crick base pairs to produce a region of double-strandedness between the two nucleic acids. Thus, adenine in one strand of DNA or RNA pairs with thymine in an opposing complementary DNA strand or with uracil in an opposing complementary RNA strand. It will be understood that each nucleotide in a nucleic acid molecule need not form a matched Watson-Crick base pair with a nucleotide in an opposing complementary strand to form a duplex.

By "mismatch" is meant that a nucleotide in one strand does not or cannot pair through Watson-Crick base pairing and π-stacking interactions with a nucleotide in an opposing complementary strand. For example, adenine in one strand would form a mismatch with adenine, cytosine, or guanine in an opposing nucleotide strand. In addition, a mismatch occurs when a first nucleotide cannot pair with a second nucleotide in an opposing strand because the second nucleotide is absent (i.e., an unmatched nucleotide).

By a "disease" is meant a condition of a living organism which impairs normal functioning of the organism, or an organ or tissue thereof.

By an "immortalized cell" is meant a cell that is capable of undergoing a substantially unlimited number of cell divisions in vivo or in vitro. One example of an immortalized cell is a cell into which (or into an ancestor of which) has been introduced an exogenous gene or gene product (e.g., an oncogene) or virus (e.g., Epstein-Barr virus) which allows that cell to divide an unrestricted number of times. An immortalized cell may also arise from a genomic mutation in an endogenous gene that gives rise to a mutated gene product or dysregulation of an endogenous gene product (e.g., a dysregulation that allows the overexpression of a cell cycle regulatory gene). An immortalized cell is distinguished from a stem cell in that an immortalized cell has an alteration affecting normal gene expression and/or regulation. Exemplary immortalized cells include cancer cell lines, such as those that have been generated from solid and non-solid tumors. Such cells are commercially available, for example, from the American Type Culture Collection (see ATCC Catalog of Cell Lines and Hybridomas, Rockville, Md.). Immortalized cells also include naturally-occurring or artificially-generated cell lines.

Other features and advantages of the invention will be apparent from the following detailed description, and from the claims.

BRIEF DESCRIPTION OF THE DRAWING

FIG. 1 is a schematic representation of the four possible alleles (1–4) for variance #1 and variance #2 located 300 nucleotides apart on a chromosomal fragment.

DETAILED DESCRIPTION

A variety of methods are described herein for the rapid and accurate detection of DNA sequence variation for research, therapeutic, or diagnostic purposes. Table I lists exemplary techniques to detect and/or resolve sequence differences, grouped according to the characteristics of the physical or enzymatic method used. All of these methods involve the formation of heteroduplexes, either between a probe and a test sample or between alleles of a test sample.

TABLE I

Methods for DNA variance detection based on heteroduplex formation

| Method | Principle | References | Sensitivity (false negatives) | Selectivity (false positives) | Probe Issues |
|---|---|---|---|---|---|
| Heteroduplex Analysis (HA); also called Conformation Sensitive Gel Electrophoresis | Heteroduplexes have altered mobility (usually they run slower) in nondenaturing acrylamide gels relative to homoduplexes, apparently due to DNA kinking at sites of mismatch. Alternative gel matrices can increase resolution. | White et al., Genomics 12: 301–306, 1992; Ganguly et al., Proc. Natl. Acad. Sci. USA 90: 10325–10329, 1993; Williams et al., Hum. Mol. Gen. 4: 309–312, 1995. | Not extensively characterized, but in general, probably 80–90% sensitive. (For example, 8 of 9 point mutations were detected by White et al.) | False positive rate appears low from published data. | Assay can be run with or without probe. Probe allows one step labelling, standardization of assay conditions, simplified interpretation of results, and serves as a control |
| Chemical cleavage of mismatches (CCM) | Mispaired nucleotides in heteroduplex DNA are accessible to base modifying reagents such as hydroxylamine, osmium tetroxide, potassium permanganate, and carbodiimide. The modified bases can subsequently be specifically cleaved with piperidine or other chemicals | Hydroxylamine & osmium tetroxide: Cotton et al., Proc. Natl. Acad. Sci. USA 85: 4397–4401, 1988; Cotton et al., Nucl. Acids Res. 17: 4223–4233, 1989; Smooker et al., Mut. Res. 288: 65–77, 1993. Carbodiimide: Novack et al., Proc. Natl. Acad. Sci. USA 83: 586–590, 1986 | Sensitivity of hydroxylamine/osmium tetroxide method is excellent, although efficiency of cleavage is not 100% or homogeneous among different sites. The carbodiimide method is not well tested | Background can be high; method is highly sensitive to cleavage conditions. | Assay can be run with or without probe. Probe allows one step labelling, standardization of assay conditions, simplified interpretation of results, and serves as a control. |
| Ribonuclease cleavage of RNA:DNA or RNA:RNA heteroduplexes | Ribonuclease A cleaves RNA:DNA heteroduplexes specifically at mismatched bases on the RNA strand. Conditions for using other RNAases have been discovered (MisMatch Detect II kit, Ambion, Inc., Austin, TX) which reportedly improve sensitivity to nearly 100%. | Myers et al., Science 230: 1242–1246, 1987; Goldrick et al., Biotechniques 21: 106–112, 1996. | Theoretically high but as a practical matter the method is subject to many artifacts and is not widely used. RNAse does not cut with equal efficiency at all mis-matches; background can be high. | Higher false positive rate than most other methods | Assay is generally performed with a probe. Probe allows one step labelling, standardization of assay conditions, simplified interpretation of results, and serves as a control. |
| Denaturing Gradient Gel Electrophoresis (DGGE) and related methods (e.g., denaturing HPLC (DHPLC) and temperature gradient gel electrophoresis (TGGE)). | Double stranded DNA or RNA fragments are resolved on the basis of conformational differences associated with partial strand melting as they migrate through a gradient of denaturant in a gel. The denaturant can be chemical, e.g., DGGE, where a gradient of formamide and urea is used, or thermal, e.g., thermal gradient gel electrophoresis (TGGE). | Abrams and Stanton, Methods in Enzymology 212: 71–104, 1992; Abrams et al. Genomics 7: 463–475, 1990; Myers et al., pp. 71–88 in Erlich, H. A. (ed.), PCR Technology: Principles and Applications for DNA Amplification, Stockton Press, New York, 1989. | Sensitivity is nearly 100% with appropriate design of GC clamps based on analysis of melting maps. Sensitivity is much lower for natural (non-clamped) sequences. | False positives are minimal | Probes are not required (sample - sample heteroduplexes will suffice) but provide advantages of speed, consistency, and ease of automation. |
| Resolvases, including T4 endonuclease VII and T7 endonuclease I, which recognize and cleave mismatches | Resolvases are enzymes that recognize and cleave branched DNA intermediates. They also recognize and cleave DNA heteroduplexes containing single base mismatches, deletions, or insertions. Resolvases have been identified in a wide variety of species. | Youil et al., Genomics 32: 431–435, 1996; Youil et al., Proc. Natl. Acad. Sci. USA 92: 87–91, 1995; Mashal et al., Nature Genetics 9: 177–183, 1995 | Sensitivity is virtually 100%, a claim supported by 86 of 86 globin mutations detected by R. Cotton (Genomics 32: 431, 1996). However, cleavage efficiency is highly variable. | False positives are minimal with optimal conditions. Impure probes result in background cleavages. | Assay can be run with or without probe. Probe allows one step labelling, standardization of assay conditions, simplified interpretation of results, and serves as a control. |
| Mismatch specific bindases, such as MutS, bind to heteroduplexes | Bindases are proteins that selectively bind heteroduplexes. Bindases can be immobilized on a solid phase and label on heteroduplexes can be detected as bound material after washing off non-bound homoduplexes. MutS is the best studied example, but there are related | Debbie, P., et al. Nucleic Acids Research 25: 4825–4829, 1997; Wagner, R., et al. Nucleic Acids Research 19: 3944–3948, 1995. | The sensitivity is reportedly high, although no systematic surveys of large well characterized mutant collections have been done. Deletions of greater than 4 bases will be missed. | The selectivity is reportedly excellent, however, signal to noise ratio is generally low (approx. 2-fold) suggesting problems with selectivity. | Assay can be run with or without probe. Probe allows one step labelling, standardization of assay conditions, simplified interpretation of results, and serves as a control. |

We have determined that it would be preferable in many instances to derive probes without cloning through the amplification of gene segments from a template of genomic DNA or cDNA. Since most genes in an individual are present in two copies, one inherited from each parent, that normally differ in their sequences at one or more positions, and the positions of all such variations are not known, it is not generally possible to derive a probe which has a unique base present at each position within the sequence. This results in a probe that can form a heteroduplex with itself, creating a variety of possible background problems for variance detection. Described herein are novel methods for producing, without cloning, probes that have unique base sequences. Such probes are useful for identifying variant sequences in genes derived from an individual.

It is known that the sequence of a specific gene differs substantially in different individuals. Estimates suggest that 1 in 100 bases to 1 in 300 bases within the sequence of a gene vary between individuals in human populations. Many variations are pathogenic mutations that cause disease, but the vast majority are non-pathogenic changes that contribute to normal human variability or the variable responses of individuals to their environment. Others may have no biological consequence. Methods for detecting variances in gene sequences have important applications both for research into the cause of disease and for medical diagnostics. Methods for detecting variances also have broad application in the fields of animal breeding and plant genetics in that variances may be discovered to be associated with phenotypes of interest.

For use in the methods described herein, a test sample (that is, a segment of genomic DNA or cDNA derived from an individual by cloning or amplification that contains a sequence of interest) is analyzed. The term "derived from an individual" refers to cells, such as blood, tissue, or cultured cells, that are obtained originally from an individual. The test sample may be derived from an individual for use in research or diagnostic testing aimed at discovering variances that exist in the population, variances that potentially represent the cause of disease, the cause of normal variation, or silent variation. In one example, the test sample may be derived from a patient with a disease, a condition, or another phenotype of interest, to determine whether that patient's gene contains variances that are associated with a particular disease, predisposition to disease, prognosis, or response to therapy. Alternatively, the test sample may be derived from a patient with or without disease symptoms to diagnose whether that patient has a disease, or a predisposition to a disease, or to assess the patient's present or further response to therapy. For research aimed at the discovery of variances and for diagnostic methods, it is preferable to have a probe with a unique sequence in order to identify variations from this reference sequence.

Variances may be detected in test samples by forming duplexes between the two parental copies present in a test sample. If the two sequences differ, heteroduplexes will be formed. This approach is less preferred for the following reasons. First, each sample must be labelled separately, increasing the likelihood of non-uniform or inadequate labelling and requiring new labelling for each new batch of test samples. Second, any sequence differences are measured against an unknown reference sequence; homozygosity for variances of interest will not be detected. And, third, there is no known hemizygous reference sample against which to compare the test samples.

A preferred method for detecting variances involves hybridizing a probe to a test sample and analyzing the resulting double stranded molecule for heteroduplexes which arise when the sequences of the probe and test sample differ at one or more positions. As described above, a heteroduplex is any double stranded DNA molecule in which the two strands differ at one or more positions. Strands form a homoduplex if the sequences of the two strands allows normal base pairing to occur at every position within the double stranded DNA molecule (i.e., G binding to C, and A binding to T). Strands form a heteroduplex when normal base pairing does not occur at one or more positions. This results when the sequence of the test sample differs from the sequence of the probe, for example, due to a transition, transversion, insertion, or deletion of nucleotides within the gene sequence. The absence of heteroduplexes reveals that the sequence of the test sample is identical to that of the probe. The presence of heteroduplexes reveals that the sequence of the test sample contains variances at one or more positions, and may also reveal the location and nature of the variance.

If the probe does not have a unique sequence, this analysis may be complicated by the formation of heteroduplexes between different probe molecules, rather than between the probe and the test sequence, thus compromising the analysis of the test samples. A probe which does not have a unique sequence and which leads to formation of heteroduplexes between different constituents of the probe population generates a background signal of noninfonnative heteroduplexes that can mask informative heteroduplexes formed between probe and test sample strands, resulting in a failure to detect true sequence variants. The unique sequence probes described herein are used to form duplexes with test samples to determine whether the sequence of the test sample is identical to the probe or whether it contains variances.

Heteroduplexes can be distinguished from homoduplexes by a variety of methods known in the art including, without limitation, methods based on the physical structures that are formed by mismatched base pairing, the altered thermal stability of heteroduplexes (DNA melting behavior) as opposed to that of homoduplexes, the recognition of mismatched bases by mismatch recognition enzymes (such as elements of the DNA repair system or resolvases), or chemical reactions with mispaired bases. These methods can utilize, for example, (i) the altered electrophoretic mobility of heteroduplexes and homoduplexes, either in a nondenaturing gel, denaturing gel, gradient denaturing gel, or by liquid chromatography, (ii) the susceptibility of heteroduplexes to binding by enzymes (e.g., MutS) that recognize heteroduplexes, or (iii) the susceptibility of heteroduplexes to cleavage by enzymes (e.g., T4 endonuclease VII) that recognize heteroduplexes. Techniques that detect altered electrophoretic mobility include heteroduplex analysis (HA), constant denaturant gel electrophoresis (CDGE), denaturing gradient gel electrophoresis (DGGE), and denaturing high pressure liquid chromatography (DHPLC). Exemplary techniques that may be used to detect binding of mismatches in heteroduplexes utilize enzymes such as *E. coli* MutS (or equivalent proteins from various species) and related DNA repair enzymes. Techniques that assay cleavage of heteroduplexes utilize enzymes such as MutS in combination with other components of the bacterial DNA nucleotide repair system such as MutH and MutL (that is, a MutHLS complex, or equivalent protein complexes from other species) or enzymes such as phage T4 endonuclease VII or phage T7 endonuclease I.

In a preferred approach for carrying out variance detection, the unique sequence probe of the invention is detectably labeled, which allows the heteroduplex, or a fragment of the heteroduplex, to be visualized by analytical equipment or imaging. Commonly, nucleotide derivatives are used in the production of the probe which facilitate the incorporation of a moiety into the probes that can be directly visualized or that participates in a reaction that creates a detectable event. Examples of detectable labels include, but are not limited to, radioactive atoms, fluorescent or chemiluminescent molecules, enzymes, or affinity ligands. Preferably, the label on the probe is used to identify heteroduplexes or homoduplexes formed by hybridizing the probe to the test sample. In an alternative approach, the detectable label may instead be incorporated into the test sample, and the detectably labeled test samples used to identify heteroduplexes or homoduplexes formed following probe hybridization.

It will be understood that the terms "probe" and "test sample" typically refer to solutions or suspensions of probes or test samples of sufficient amount and sufficient concentration to form and detect double stranded heteroduplexes and homoduplexes. As known in the field of genetic variance detection, such analysis may require amounts of material ranging from 1 pg to 1 μg per reaction, representing as many as $10^6$ to $10^{12}$ molecules per reaction, where each reaction involves the mixture of a probe and a test sample to form heteroduplexes or homoduplexes. It is preferable to produce probes in sufficient quantity to allow one batch of probe to be used to assay a large number of test samples, for example, more than 100, or preferably more than 1,000 or even 10,000 test samples. This simplifies standardization of the procedures and improves efficiency for research or diagnostic applications.

The large amount of material required for generating probes is most commonly produced from a cloned segment of genomic DNA or cDNA corresponding to the gene to be analyzed. This may involve, for example, making a preparation of plasmid or M13 and preparing the probe by restriction digestion, polymerization, or PCR amplification using the clone as a template. This requires having a cloned version of a gene to be analyzed. When the goal is to analyze many different DNA sequences, the isolation of cloned versions of all the sequences may be inefficient. This is particularly true if the sequences to be analyzed are cDNAs, or long segments of genomic DNA. In the former case it may be technically difficult to obtain a full length cDNA clone; in the latter case, many different contiguous segments would need to be successfully cloned.

We have determined that it would be advantageous to have probes that may be reliably produced from a genomic DNA or cDNA template. However, materials produced by PCR amplification of the genomic DNA or cDNA template from normal cells or tissues of any particular individual contain sequences derived from two different gene copies (e.g., maternally and paternally derived) that commonly differ at one or more positions and are therefore not optimal for use as probes. As described above, the presence of heteroduplexes formed within such probe material interferes with the detection of heteroduplexes formed with the test sample. It should be emphasized that any material derived from an individual who has two copies of a gene may be presumed not to represent a unique sequence given the high frequency of genetic variances in the population. While an individual may be said to be homozygous by having the same sequence at certain positions, in virtually all cases, the gene will not be identical at all positions, and it may be presumed that a probe developed from a template of genomic DNA or cDNA from such an individual would not be unique at all or substantially all nucleotide bases.

We have determined that probes may be reliably produced from genomic DNA or cDNA segments from cells that contain only one parental copy of the gene to be analyzed, for example, by PCR amplification. Furthermore, we have identified classes of tissues and cells, as well as specific cells derived from tumors, tumor cell lines, or hybrid cell lines, that contain only one allele of the gene to be analyzed and in which the template of genomic DNA (or a cDNA thereof) comprises a single parental copy of the gene sequence and provides a probe with a unique base at each position.

In one example, the template may be derived from one copy of a gene, chromosomal segment, or chromosome remaining in a cell (either maternal or paternal) after loss of the heterologous gene, chromosomal segment, or chromosome. Similarly, the template may be derived from more than one copy of a gene, chromosomal segment, or chromosome present in a cell, each gene, chromosomal segment, or chromosome being derived from a single parental copy (either maternal or paternal).

It should be noted that it is not necessary that the tissue, cell line, or tumor have a single copy of the chromosome or chromosomes to be used for probe generation (i.e., it need not be haploid). Often tumors or cell lines, when reduced to one copy of a chromosome, duplicate that one copy so that, while no longer haploid, they remain hemizygous at all locations on the duplicated chromosome or chromosome fragment, meaning that only one version of the chromosome is present. Duplication of a single chromosome in such instances to create, for example, two copies of a chromosome is distinct from having two different chromosomes that may be homozygous for certain sequences. In contrast, duplicated chromosomes in hemizygous cells may be presumed to have unique sequences.

We use the term "gene" to refer to a sequence of DNA that includes both coding and noncoding regions. The term "allele" refers to one specific form of a gene within a cell or within a population, the specific form differing from other forms of the same gene at one, and frequently more than one, variant site within the gene sequence. The sequences at the variant sites that differ between different alleles are termed "variances," "polymorphisms," or "mutations." In general, normal cells contain two alleles of each gene, with one allele inherited from each parent.

The term "template" refers to a source of material that is the substrate for preparation of a probe using an amplification reaction. For example, a probe having a unique sequence can be made by amplifying, as a template, a hemizygous chromosome. Methods for amplification include, without limitation, polymerase chain reaction, ligase chain reaction, NASBA, SDA, 3SR, and TSA. It will be understood that, in any given method for generating a probe having a unique sequence, one or several amplification methods may be employed.

A second method for generating a probe having a unique sequence is to prepare nucleic acid from a hemizygous cell, and to use this nucleic acid to produce the probe. For example, cDNA may be generated from the RNA of a hemizygous cell and used to create a cDNA library according to standard molecular biology techniques (see, e.g., Ausubel et al., *Current Protocols in Molecular Biology*, John Wiley & Sons, New York, 1997; Sambrook et al., *Molecular Cloning, A Laboratory Manual*, 2nd ed., Cold Spring Harbor Press, Cold Spring Harbor, N.Y., 1989). The probe may then be generated from the library by a variety of methods including, without limitation, restriction endonuclease digestion, polymerase chain reaction, or the amplification methods cited herein. This method is particularly useful if the probe is from a hemizygous cell that is not an immortalized cell.

In other variations for producing a probe having a unique sequence, the template may be genomic DNA or cDNA derived from a cell or tissue in which the gene of interest is present in a single parental copy. Another template may be genomic DNA or CDNA derived from a cell or tissue in which a chromosome fragment containing the gene of interest is present in a single parental copy. The template may also be genomic DNA or cDNA derived from a cell or tissue in which one or more chromosomes containing genes of interest are present in single parental copies. Preferably, at least one chromosome, more preferably at least 5 chromosomes, yet more preferably, at least 15 or 20 chromosomes, and, most preferably, all autosomal chromosomes are present in a single parental copy in a cell used for probe production. Probes for genes present on the X chromosome or Y chromosome may be derived from templates of genomic DNA and CDNA derived from a cell line or tissue that has only one parental copy of the X chromosome and one parental copy of the Y chromosome (e.g., male cell lines or tissues). Ideally the cell line or tumor has a complete set of chromosomes derived from one parent, since in that case one source can be used to produce a probe for any DNA or cDNA segment, regardless of its chromosomal location. This is particularly useful in cases where the chromosome location of the probe sequence is not known. Alternatively, two or more cell lines may, between them, be hemizygous for all of the chromosomes of the species of interest.

Another cell or tissue from which the template is derived may contain genes from species other than humans in addition to the human gene that is the template for producing a probe (such as a somatic cell hybrid). For example, the cell may contain a complete set of genes from a species other than humans and one or more human chromosome segments or chromosomes. Preferably, the cell contains more than one human chromosome, more preferably, at least 5 human chromosomes, yet more preferably, at least 15 or 20 human chromosomes, and, most preferably, all human autosomal chromosomes present in a single parental copy. The cell may also contain one copy of the human X chromosome or one copy of the human Y chromosome. In examples of preferred somatic cell hybrids, the non-human genes are of mouse or Chinese hamster origin.

It will be apparent that the methods described herein are also applicable to analysis of genes from other species using, as sources for templates, cells or tissues that have only one parental copy of one or more genes from that species. For example, these techniques may be employed to create a bovine probe with a unique sequence, which may then be used to identify variant sequences in bovine genes. Such variant bovine sequences may be used for research, therapeutic, or diagnostic methods related to diseases in cattle (e.g., brucellosis). Similar approaches may also be used for veterinary techniques involving other livestock or domestic pets. Examples of hemizygous cell lines from other species are known in the art (Li et al, Mol. Mar. Biol. Biotechnol. 3(4):217–227, 1994; Bostock, Exp. Cell. Res. 106(2):373–377, 1977).

As applied to humans, a number of hemizygous cells and tissues may be used to provide suitable templates for genomic DNA or cDNA for producing probes having unique sequence. There now follow exemplary sources for hemizygous probe production and exemplary mismatch detection techniques. These examples are provided for the purpose of illustrating the invention and should not be construed as limiting.

Gestational trophoblastic tumors which are derived from a single germ cell.

Complete hydatidiform moles (CHM) are commonly derived from a single germ cell. While the cells of a CHM commonly contain two copies of each chromosome, both copies are derived from the same parent—nearly always the father. Most CHMs (approximately 70%) are derived from a single sperm which presumably undergoes duplication after fertilization of an empty, or a nuclear egg. Choriocarcinomas are malignant gestational trophoblastic tumors believed to arise, in at least some cases, from CHMs. Most choriocarcinomas are genetically heterozygous; however, there are reports of completely homozygous choriocarcinomas (Fisher et al., Br. J. Cancer 58: 788–792, 1988). DNA or RNA prepared from CHMs or choriocarcinomas may be used to prepare monoallelic DNA or cDNA probes (i.e., probes derived from a single allele and therefore having unique sequence) by the methods described above. Alternatively, cell lines derived from such tumors may be used to provide a more convenient, easily accessible, and inexhaustible supply of DNA or RNA. A number of cell lines have been established from choriocarcinomas and are described, for example, in Nakamura and Yamashita (Nippon Sanka Fujinka Gakkai Zasshi 38: 477–484, 1986). Some choriocarcinoma cell lines have been characterized cytogenetically or using RFLP or other DNA markers and have been found to be heterozygous; other choriocarcinoma cell lines have not yet been tested. Several cell lines have been developed from CHMs as well, but there are no reports of cytogenetic or molecular characterization of these cells.

Ovarian teratomas that are derived from a single germ cell.

Benign ovarian teratomas are entirely maternal in their derivation, and most commonly have a normal karyotype of 46,XX. It is estimated that as many as 65% of teratomas (Surti et al., Amer. J. Hum. Gen. 47: 635–643, 1990) are derived from a single maternal germ cell after failure of meiosis II (type II teratomas) or endoreduplication of a mature ovum (type III teratomas). Such teratomas are hemizygous for all loci in the genome, containing only one copy of the chromosomes normally present in the mother. Either tissue or cell lines established from such teratomas may be used as templates for DNA or RNA for preparation of monoallelic DNA or cDNA probes.

Leukemias or leukemia cell lines with near haploid karyotypes, or that have passed through a stage of near haploidy.

Up to 10% of acute myeloid leukemias in blast phase, as well as some acute lymphocytic leukemias, undergo a characteristic transformation to near haploidy (see, for example, Gibbons et al., Leukemia 5(9):738–743 1991). In some cases, there are multiple copies of the haploid chromosome set, meaning that, while only one parental copy is preserved in the cell, this chromosome may be present in several copies. Either purified tumor cells or cell lines established from such tumors may be used as a source of DNA or RNA for preparation of monoallelic probes (i.e., probes with unique sequences) for loci on all chromosomes except any retained diploid chromosomes. The problem of diploidy for some chromosomes may be overcome by using several cell lines with non-overlapping diploid chromosomes to make probes. Several immortal cell lines with the desired properties have been described. For example, Kohno et al. (J. Natl. Cancer Inst. 64: 485–493, 1980) have described a cell line called NALM-16, which was established from an acute lymphoblastic leukemia in which only three chromosomes, chromosomes 14, 18, and 21, were disomic at one point in the evolution of the leukemia. In addition, Andersson et al. (Leukemia 9(12): 2100–2108, 1995) have described a cell line, KBM-7, which is diploid for only two chromosomes, chromosomes 8 and 15. Together, these two cell lines are useful for preparing monoallelic probes from any position in the genome.

Solid cancer cell lines with near haploid karyotypes, or that have passed through a stage of near haploidy.

Near-haploid karyotypes have been reported in a variety of non-leukemic malignancies, including squamous cell lung cancer (having 27 chromosomes), endometrioid cancer of the ovary (having 29 chromosomes), malignant fibrous histiocytoma, and renal oncocytoma. A cell line has been established from the lung cancer specimen (described in Drouin et al., Genes, Chromosomes, and Cancer 7: 209–212, 1993), and is diploid for only chromosomes 5, 7, 22, and the X chromosome. Either purified tumor cells or cell lines established from such tumors are useful as sources of DNA or RNA for preparation of monoallelic DNA or cDNA probes (i.e., probes having unique sequences) for loci on all chromosomes except any retained diploid chromosomes.

Individual Germ Cells

Another example of a cell haploid for all human chromosomes is an individual germ cell (i.e., a sperm cell or an oocyte). PCR products from, for example, a single sperm cell may be generated and labeled to produce probes having unique sequences (see, for example, Li et al., Proc. Natl. Acad. Sci. 87: 4580–4584, 1990). Alternatively, a whole genome amplification procedure using, for example, primer extension preamplification (PEP; for example, as described in Zhang et al., Proc. Natl. Acad. Sci. 89: 5847–5851, 1992; and Casas and Kirkpatrick, Biotechniques 20: 219–225, 1996) may be employed to generate an amplified representation of the sequences in the single sperm cell (or any other single haploid cell, such as an oocyte). From the resulting amplified representation, multiple subsequent amplifications may be performed to generate a variety of different unique sequence probes. This approach greatly reduces the effort involved in generating large numbers of unique sequence probes. Similar methods may be applied to oocytes (Cui et al., Genomics 13: 713–717, 1992) and to single somatic cells (Snabes et al., Proc. Natl. Acad. Sci. 91: 6181–6185, 1994), for example, those somatic cells described below.

Somatic cell hybrids that are monosomic for one or more human chromosomes.

A different approach to the isolation of cell lines that are haploid for human chromosomes is the use of somatic cell hybrids. These are produced by fusing human cells or micronucleated chromosomes to nonhuman recipient cells, usually hamster or mouse cell lines. This may be achieved by transferring a single human chromosome to the nonhuman recipient cell, or by selecting hybrid cell lines in which only a single human chromosome is retained. A collection of such cell lines, each retaining a different human chromosome, has been assembled at the Coriell Cell Repository (Coriell Institute for Medical Research, Camden, N.J.; see pages 703–743 of their 1994/1995 Catalog of Cell Lines for a description of these cell lines). The human genes are typically expressed in such hybrids, enabling the isolation of either monoallelic DNA or cDNA using, for example, standard amplification procedures.

Preparation of probes by amplification of single copy genes.

Once a cell is determined to have only one allele of a gene (or fragment thereof) or chromosome (e.g., a hemizygous cell or a somatic cell hybrid), a probe may be prepared from this monoallelic gene or chromosome by any number of standard techniques known in the art (see, e.g., Ausubel et al., supra; Sambrook et al., supra). Particularly useful probes of the invention are labelled. In one exemplary method, to generate a rhodamine-labelled probe, RNA is collected from the cell, cDNA is prepared from the RNA (using, e.g., the Universal RiboClone cDNA synthesis kit from Promega, Madison, Wis.), and the following PCR protocol is employed.

According to this technique, fluorescently labeled probes with high specific activity are produced by incorporation of rhodamine labeled dUTP into a DNA fragment during PCR. The concentration of rhodamine labeled dUTP can be varied to achieve different degrees of fluorescent labeling. Methods for optimizing PCR reactions are well known in the art of molecular biology and include testing various temperatures for the annealing step of the PCR, changing the $MgCl_2$ concentration, and changing primer and template concentrations. One example of a PCR protocol for use in a variance detection system utilizing T4 endonuclease 7 is as follows.

A 500 $\mu$l PCR reaction is set up which contains Taq buffer (1× from a 10× stock; 10× PCR stock contains 100 mM Tris pH8.3, 500 mM KCl, and 0.1% gelatin), 200 $\mu$M (final concentration) each dNTP, 2.5 mM (final concentration) $MgCl_2$, and 12.5 units of AmpliTaq Gold (Perkin-Elmer Corp., Norwalk, Conn.), 1 $\mu$M (final concentration) forward primer, 1 $\mu$M (final concentration) reverse primer, 5 $\mu$M (final concentration) dUTP Rhodamine (2.5 $\mu$l of Molecular Probes Catalog No. C-7629, Eugene, Oreg.), distilled water, and 1.25 $\mu$g of cDNA or DNA derived from the hemizygous cell. The amount of cDNA required will vary depending on the expression levels in the hemizygous cell of the gene of interest being amplified. The pH of the Taq buffer and the concentrations of $MgCl_2$ and KCl may differ from probe to probe depending on the PCR optimization conditions.

The reaction mix is then divided into 5 PCR tubes, such that each tube contains 100 $\mu$l. The DNA is amplified using a PCR machine (e.g., a Perkin Elmer 9600) using, for example, the following cycle parameters: 95° C. for 12 minutes; then 30 cycles of: 94° C. for 20 seconds, optimal annealing temperature for 30 seconds, 72° C. for 45 seconds; followed by: 72° C. for 12 minutes; and then holding at 4° C. The optimal annealing temperature for each probe is determined by an initial PCR optimization procedure and may differ between probes.

The probe reaction mixtures are combined into one tube (0.5 ml total) and added to 1.5 ml of TE buffer (10 mM Tris pH 8.0, 1 mM $Na_2EDTA$). The 2 ml mixture is then added to a Centricon-50 cartridge (Amicon Inc., Beverly, Mass.) and centrifuged in a Sorvall SS-34 rotor at 5500 rpm for 15 minutes. The filters are washed by adding 2 ml of TE buffer to the cartridge and centrifuging at 5500 rpm for 15 minutes, and repeating for a total of three washes. The Centricon-50 filters are then inverted, and the labeled PCR product (i.e., the probe) recovered by centrifuging at 2000 rpm for 2 minutes. (The flowthrough volume at the bottom of the cartridge contains the recovered probe.) The $OD_{260}$ and $OD_{280}$ is read to determine the concentration of the probe recovered from the filter. Serial dilutions (1:2) of the probe are then made, and the fluorescence measured by electrophoresis on an automated DNA sequencer (e.g., an ABI 377 sequencer), capillary electrophoresis/laser induced fluorescence instrument, or a similar device with detectors tuned to the emitting wavelength of the fluorophore. This information is then used to calculate the specific activity of the probe (fluorescence incorporation per femtomole of PCR product), which can then be mixed with a sample in an amount sufficient for the detection of probe-sample heteroduplexes.

Method of determining whether a gene is present in a single parental copy.

In general, there are two preferred methods for determining if a cell line contains only one allelic form of a gene, and is therefore suitable for making monoallelic probes having a unique sequence which are useful in the invention. The two methods are applicable in different situations. A cell that has only one copy of a gene or chromosome can best be identified by cytogenetic or molecular analysis. A cell that has more than one copy of a single allelic form of a gene can best be identified by molecular analysis.

I. Gene is Present in a Single Copy in a Cell

Cytogenetic analysis can reveal the number of copies in a cell of a specific DNA sequence or of a collection of DNA sequences (for example, a collection of DNA sequences spread over an entire chromosome). The methods for cytogenetic analysis are well know in the art (see, for example, Chapter 4 of Dracopoli, N. et al., *Current Protocols in Human Genetics*, John Wiley and Sons, 1997, and references cited therein). Briefly, the steps for cytogenetic analysis are as follows: (i) arrest dividing cells in interphase or metaphase with mitosis blocking drugs such as colchicine; (ii) make the cells permeable to DNA probes (for interphase studies), or make a chromosome spread by dropping cells on glass slides; (iii) hybridize labelled denatured DNA corresponding to a DNA segment or segments (which could represent a gene, chromosome, or other segment of interest); (iv) wash off unhybridized probe; and (v) visualize the probe-bound molecules using microscopy. The DNA or chromatin is stained to allow visualization of the probe in the context of the chromosomes.

A variety of image enhancing methods can be used to aid visualization of the bound probe. Probes are often labelled with fluorescent tags and used in a technique that is referred to as fluorescent in situ hybridization, or FISH (Speicher, M. R. et al., Nature Genetics 12: 368–375, 1996). Since the labelled probe hybridizes to each cellular copy of the target DNA segment, the number of copies of the target gene can be determined by simply counting the number of hybridizing spots. FISH has been used extensively to count the number of copies of specific sequences or chromosomes (Barks, J. H. et al., Genes Chromosomes Cancer 19: 278–285, 1997; El-Naggar, A. K. et al., Human Pathology 28: 881–886, 1997). When one or more chromosomes from a cell line are shown to be present in one copy, that cell line can then be used to prepare monoallelic probes for any gene located on the single copy chromosome or chromosomes. Virtually all near-haploid tumor cell lines described in the literature have been identified by karyotyping.

II. Gene is Present in Multiple Copies in a Cell

In order to be suitable for the production of monoallelic probes, it is not necessary that a cell contain a gene in a single copy; all that is required is the presence of a single allelic form of the gene in the cell or population of cells. Hence, some cells may have two or more copies of the same gene, chromosome, or set of chromosomes. This can occur by aberrant fertilization, as in the case of hydatidiform moles, where two copies of the same paternal chromosome set are often found. Alternatively, it can occur in cancers as a result of chromosome nondisjunction, or partial or complete chromosome deletion, followed by duplication (sometimes called endoreduplication) of the remaining chromosome or chromosomes. Other instances when this occurs are described herein. In order to determine if such a cell contains only one allelic form of a gene or genes or other DNA segment, it is best to use molecular techniques.

Molecular analysis can reveal the presence of different copies of a specific DNA sequence that is polymorphic (i.e., known to vary in a population). The absence of two polymorphic forms in a cell indicates that at the sampled site the cell contains only one allelic form, or is homozygous at that site. The demonstration of homozygosity at many sites located on the same chromosome is evidence of homozygosity for a region of a chromosome, or for an entire chromosome. For example, consider a cell or tissue sample that has been genotyped at 25 known sites of DNA sequence variation, all mapped to the same chromosome and known to be distributed along the length of the chromosome. If, in a normal population, 50% of subjects are heterozygotes at each of the 25 sites, but in the genotyped sample all 25 sites are homozygous, then it is extremely likely that the sample has only one allelic form of every gene on the tested chromosome, regardless of the number of chromosomal copies in each cell. Specifically, the likelihood of finding a cell homozygous for all 25 markers, given that each is heterozygous in 50% of individuals, is 2 to the 25th power ($2^{25}$), or one in 33,554,432.

Many polymorphic DNA markers have been identified in man and may be used to perform the genotyping analysis (see, for example, the Genethon human genetic linkage map, published as an appendix to Dib et al., Nature 380: 152–154, 1996). The ideal candidate polymorphic sites are sites that can be assayed by polymerase chain reaction (PCR), and that are highly polymorphic. Short tandem repeat polymorphisms (STRs) are di-, tri-, or tetra-nucleotide sequences (for example the di-nucleotide CA) that repeat for a variable number of times in different alleles. They can be tested by PCR amplification of the STR using flanking primers in unique sequence, followed by gel electrophoresis to resolve alleles by size. PCR allows the use of small amounts of sample DNA and the automation of genotyping. Other polymorphic DNA markers that may be used for genotyping include restriction fragment length polymorphisms (RFLPs) and variable number of tandem repeat polymorphisms (VNTRs). Methods for genotyping DNA samples using these types of DNA markers are provided in Dracopoli, N. et al. (*Current Protocols in Human Genetics*, John Wiley and Sons, 1997; see, in particular, Chapter 2).

Variance Detection by SSCP.

One technique commonly employed in the identification of single nucleotide differences is the single strand conformation polymorphism (SSCP) method (Orita et al., Genomics 5: 874–879, 1989). This methodology is effective for scanning PCR products for sequence variants, and is a standard technique in human genetics for variance detection, with numerous studies of its efficacy (greater than 90% with optimized protocols) and schemes for improved throughput. The probes of the invention are useful in the SSCP method because they provide good controls, since the probe will give rise to only one allelic form of the sequence being analyzed. The band or bands produced from a single allele are often useful in interpreting more complex patterns of bands produced from heterozygous samples, because it is possible to determine unambiguously which molecular species are derived from each allele in the heterozygous sample. Likewise, samples from the cells described herein are also useful in the SSCP technique, since it is helpful to have samples with known alleles for probe production.

Variance detection by DGGE.

Denaturing gradient gel electrophoresis (DGGE) represents a preferred technique for the identification of DNA sequence variances in genomic DNA or cDNA, or in PCR products amplified from genomic DNA or cDNA. The DGGE method was originally described by Fischer and Lerman ("Two Dimensional Electrophoretic Separation of Restriction Enzyme Fragments of DNA," Methods in Enzymology 68: 183–191, 1979; "DNA Fragments Differing by Single Base-Pair Substitutions are Separated in Denaturing Gradient Gels: Correspondence with Melting Theory," Proc. Natl. Acad. Sci. U.S.A. 80:1579, 1983) and has been improved since by many investigators (see, for example, Myers et al., "Mutation Detection by PCR, GC-Clamps, and Denaturing Gradient Gel Electrophoresis," (pp. 71–88) in Erlich, H. A. (ed.), *PCR Technology: Principles and Applications for DNA Amplification*, Stockton Press, New York, 1989; Myers et al., "Detecting Changes in DNA: Ribonuclease Cleavage and Denaturing Gradient Gel Electrophoresis," (pp. 95–139) in Davies, K. E. (ed.): *Genomic Analysis: A Practical Approach*, IRL Press Ltd., Oxford, 1988; and Abrams and Stanton Jr., Methods in Enzymology 212: 71–104 1992).

The basic principal of DGGE involves the creation of a gradient of denaturant in a gel, which is then used to resolve double stranded DNA (or RNA) fragments on the basis of conformational differences associated with strand melting. The denaturant can be chemical (as in DGGE, where a gradient of formamide and urea is typically used) or thermal (as in a related technique called thermal gradient gel electrophoresis, or TGGE, where a gradient of heat is used). To obtain conditions where double stranded DNA is close to melting, DGGE gels are immersed in a heated bath of electrophoresis buffer, while TGGE gels have a fixed concentration of chemical denaturant.

As a double stranded DNA molecule migrates through a DGGE gel from a low concentration of denaturant at the origin to higher concentrations of denaturant toward the end of the gel, it eventually reaches a level of denaturant that will cause partial melting. Some design of DNA molecules (e.g., addition of a GC clamp) is often necessary to assure that the partial melting will occur as desired. The concentration of denaturant required to melt a given DNA segment is highly sensitive to sequence differences in the DNA, including changes as subtle as a single nucleotide substitution. Partially melted DNA fragments move through gels at a much slower rate than their fully duplex counterparts. Thus, two DNA fragments differing at a single nucleotide can be distinguished on the basis of their gel position after an appropriate period of electrophoresis; the fragment with the more stable structure (resulting from, for example, a G:C base pair in place of an A:T pair) will travel further in the gel than its less stable counterpart, because it will encounter the concentration of gradient required to melt it (and consequently dramatically retard or nearly stop its movement) at a point further along in the gel.

The DGGE method reveals the presence of sequence variation between individuals as shifts in electrophoretic mobility, but does not show the sequence itself. Direct sequencing of DNA fragments (from different individuals) with altered mobility in the DGGE assay will reveal the precise sequence differences among them (see, e.g., Ausubel et al., supra for standard sequencing techniques). From the nucleic acid sequence data, the amino acid sequence can be determined, and any amino acid differences can be identified.

The DGGE method is suitable for analysis of restriction enzyme digested genomic DNAs, as initially described by Lerman and co-workers (supra) and later extended (Gray, M., Amer. J. of Human Genetics 50: 331–346, 1992). DGGE is equally suitable for analysis of cloned DNA fragments or DNA fragments produced by PCR. The analysis of cloned fragments or PCR fragments has the advantage that non-natural sequences, rich in and C nucleotides, can easily be added to the 5' ends (either flanking the cloning site or at the 5' ends of PCR primers). Such DNA fragments have very stable double stranded segments, called GC clamps, at one or both ends. The GC clamps alter the melting properties of the fragments, and can be designed to insure melting of the inter-primer segment of the PCR product at a lower temperature than the clamps, thereby optimizing the detection of sequence differences (see Myers et al., supra and Myers et al., Nucleic Acids Research 13: 3131, 1985). GC clamps can be rationally designed for any specific DNA fragment of known sequence by use of a computer program (e.g., the MELT94 program written by L. Lerman and used in Michikawa et al., Nucl. Acids Res, 25(12):2455–2463, 1997) that accurately predicts melting behavior based on analysis of primary sequence. When GC clamps are used correctly, the DGGE method is highly efficient at detecting DNA sequence differences. Not only are nearly 100% of differences detected, but the false positive rate is essentially zero (Abrams, E. S. et al., Genomics 7: 463–475, 1990). Recently, methods for increasing the throughput of DGGE have been developed, based on multiplex PCR.

In general, the steps for carrying out DGGE with GC clamps are as follows.

1. Design DNA fragments with optimal melting behavior. Oligonucleotide primers are selected, using GC clamps as necessary, to produce a single melting domain over the length of the sequence to be analyzed. It may be necessary to divide the sequence into overlapping fragments to achieve this goal. Design of primers and simulated analysis of fragments can be performed with the computer program described by Lerman (Lerman and Silverstein, Methods in Enzymology 155: 482–501, 1987). The output of the program is the melting map of the fragment, from which it will also be possible to determine the optimal range of denaturant in the gradient and the approximate electrophoresis time for fragments to reach the point of melting in the gradient.

2. Amplify testfragments by PCR. Procedures for optimizing PCR are briefly described in the specification and are well known in the art. Template DNA samples may either be cDNA or genomic DNA and are typically drawn from a panel of unrelated individuals.

3. Prepare a probe fragment and form heteroduplexes between probe and sample. The use of probes has the advantage that all the test samples are compared to a single reference sample (often of known sequence) simplifying analysis of results; the probe also serves as a standard or marker for the mobility of a specific allele (since mobility of fragments in DGGE is not proportional to length it can be difficult to identify fragments with certainty). If samples are labelled, use of a probe allows one labelling procedure to be used for a large number of samples. PCR is the best way to prepare probes because a GC clamp can be attached to the sequence to be analyzed using a long primer. Template DNA samples can either be cDNA or genomic DNA. Optimally, the probe will be produced from a hemizygous or cloned template, insuring that the probe represents a single unique sequence.

4. Pour a denaturing gradient gel. Briefly, two gel solutions are made containing the desired beginning and end concentrations of denaturant. The gel solutions are generally made by mixing "0%" and "100%" denaturant stock solutions, where the 0% stock consists of 7% acrylamide in Tris-acetate EDTA (TAE) electrophoresis buffer, and the 100% stock is also 7% acrylamide in TAE, plus 40% formamide by volume and seven molar urea. Equal volumes of the two solutions (e.g., twelve milliliters of each solution) are poured into the two chambers of a gradient maker (usually between 20 and 40% denaturant in the upstream chamber and 60 to 80% in the lower one) immediately after addition of ammonium persulfate and TEMED for acrylamide polymerization. The gradient gel can then be poured by opening the stopcock of the gradient maker. Usually gels are 0.75 to 1 mm in thickness, and gel combs that form 10–30 wells are used. With commercially available apparatus multiple gradient gels can be poured simultaneously. Suitable apparatus is sold by several vendors, including the BioRad (Hercules, Calif.) Decode system and the C.B.S. Scientific DGGE system.

5. Place the gel in a heated bath of electrophoresis buffer. Gels are electrophoresed at elevated temperature which, together with the denaturant, brings the DNA fragments to their melting point. Gels are often run at 60° C. in 1× TAE buffer, with constant recirculation of buffer to the upper buffer chamber. Once the gel has been placed in the heated tank and allowed to equilibrate it can be loaded. Multiple gels can be run simultaneously in the same tank with the apparatus listed above.

6. Load and run gel. Enough PCR product from each sample may be loaded on the gel so that samples can be detected by a simple DNA staining procedure, thereby avoiding use of radioactivity, dyes or hybridization procedures. To achieve this, at least 100 ng of each sample should be loaded, but preferably over 200 ng. Gel running conditions can be estimated from the output of the MELT87 program (used in Desbois et al., Hum. Mutat. 2(5): 395–403, 1993), however empirical adjustment are often necessary. Usually a voltage of approximately 80 V to 200 V is applied for periods of 5–20 hours, depending on the characteristics of the fragments being analyzed.

7. Stain and analyze gel. After electrophoresis, gels are stained with, for example, ethidium bromide, SYBR Green, or silver. The location of PCR products produced with the same primer pairs is compared. Altered location, and usually the appearance of two or more bands instead of one, signifies the presence of DNA sequence differences. More than two bands from a diploid sample are often present because, during the terminal cycle of heating and cooling of the PCR step, heteroduplexes are formed between the maternally and paternally inherited alleles. If those alleles differ in sequence, the heteroduplexes will have mispaired nucleotides at the sites of difference. As a result, the heteroduplexes will be less stable than either of the homoduplex species, and will consequently melt and be retarded in the gel at a lower concentration of denaturant. Altogether, one may see four bands in such samples: two reciprocal heteroduplexes and two homoduplexes. The specific pattern of fragments in each lane constitutes a signature for a specific nucleotide change.

8. Sequence DNA fragments with altered mobility. Examples of all different signatures are next analyzed by DNA sequencing to identify the base difference(s) accounting for altered mobility in the gradient gel. Sequencing is performed according to standard techniques.

Variance detection using a T4 endonuclease VII mismatch cleavage method.

The enzyme, T4 endonuclease VII, is derived from the bacteriophage T4. T4 endonuclease VII is used by the bacteriophage to cleave branched DNA intermediates which form during replication so that the DNA can be processed and packaged. T4 endonuclease can also recognize and cleave heteroduplex DNA containing single base mismatches as well as deletions and insertions. This activity of the T4 endonuclease VII enzyme can be exploited to detect sequence variances present in the general population.

In one particular approach to the identification of sequence variations using a T4 endonuclease VII mismatch cleavage assay, 400–600 bp regions from a candidate gene are amplified in a panel of DNA samples (for example, cDNA or genomic DNAs representing some cross section of the world population), for example, by the polymerase chain reaction, and are mixed with a labeled probe. Heating and cooling the mixtures allows heteroduplex formation between the probe and sample DNA. To this mixture is added T4 endonuclease VII, which will recognize and cleave at sequence variance mismatches formed in the heteroduplex DNA. Electrophoresis of the cleaved fragments, for example, on an automated DNA sequencer may be used to determine the site of cleavage. To more specifically pinpoint the variance site, a subset of the PCR fragments identified by T4 endonuclease VII cleavage as containing variances may be sequenced in the region of cleavage to establish the specific location and nature of the base variation.

For carrying out the above detection method, a candidate gene sequence may be downloaded from an appropriate database, and primers for PCR amplification may be designed which result in the target sequence being divided into amplification products of between 400 and 600 bp. Preferably, there will be a minimum of a 50 bp overlap (not including the primer sequences) between the 5' and 3' ends of adjacent fragments, to ensure the detection of variances which are located close to one of the primers.

Optimal PCR conditions for each of the primer pairs are determined experimentally. Parameters including, but not limited to, annealing temperature, pH, $MgCl_2$ concentration, and KCl concentration may be varied until conditions for optimal PCR amplification are established. The PCR conditions derived for each primer pair are then used to amplify a panel of DNA samples (cDNA or genomic DNA) which is chosen to best represent the various ethnic backgrounds of the world population or some designated subset of that population, for example, a population with a specific disease or therapeutic response.

For variance detection, one DNA source is chosen to be used as a probe. Optimally this DNA source should be one of the sources of unique sequence DNA described above. The same PCR conditions used to amplify the panel are used to amplify the probe DNA. However, a labeled nucleotide (such as a fluorescently labeled nucleotide) is included in the deoxynucleotide mix, such that a percentage of the incorporated nucleotides will be fluorescently labeled. The labeled probe is mixed with the corresponding PCR products from each of the DNA samples, and then heated and cooled rapidly to allow the formation of heteroduplexes between the probe and the PCR fragments from each of the DNA samples. T4 endonuclease VII is added directly to these reactions and allowed to incubate for 30 minutes at 37° C. 10 μl of a formamide loading buffer is then added directly to each of the samples, which are then denatured by heating and cooling.

A portion of each sample is electrophoresed, for example, on an ABI 377 sequencer or by capillary electrophoresis. If there is a sequence variance between the probe DNA and the sample DNA, a mismatch will be present in the heteroduplex fragment formed. The enzyme T4 endonuclease VII will recognize the mismatch and cleave at the site of the mismatch. This will result in the appearance of two peaks corresponding to the two cleavage products when run on the ABI 377 sequencer. If there are two differences between probe and sample, then there will be two cleavages, resulting in three fragments, and so on.

Fragments identified as containing variances are subsequently sequenced using conventional methods to establish the exact location and nature of the variance.

Other methods for carrying out T4 endonuclease VII assays are described for example, in Cotton et al., U.S. Pat. No. 5,698,400 and Babon et al., U.S. Ser. No. 08/545,404.

Use of Hemizygous Probes for Haplotyping

In any diploid cell, there are two haplotypes at any gene or other chromosomal segment that contain at least one distinguishing variance. In many well-studied genetic systems, haplotypes are more powerfully correlated with phenotypes than single nucleotide variances. Thus, the determination of haplotypes is valuable for understanding the genetic basis of a variety of phenotypes including disease predisposition or susceptibility, response to therapeutic interventions, and other phenotypes of interest in medicine, animal husbandry, and agriculture.

In samples of DNA or cDNA derived from tissues or cells that have two chromosomes (i.e., all normal somatic tissues in humans and animals) in which there are two or more heterozygous sites, it is generally impossible to tell which nucleotides belong together on one chromosome when using genotyping methods such as (i) DNA sequencing, (ii) nucleic acid hybridization of oligonucleotides to genomic DNA or total cDNA or amplification products derived therefrom, (iii) nucleic acid hybridization using probes derived from genomic DNA or total cDNA or amplification products derived therefrom, or (iv) most amplification-based schemes for variance detection.

Haplotypes can be inferred from genotypes of related individuals by using a pedigree to sort out the transmission of groups of neighboring variances, but pedigree analysis is of little or no use when unrelated individuals are the subject of investigation, as is frequently the case in medical studies. There are some methods for determining haplotypes in unrelated individuals, for example, methods based on setting up allele-specific PCR primers for each of two variances that are being scanned (Michalatos-Beloin et al., Nucl. Acids Res. 24: 4841–4843, 1996); however, these methods generally require customization for each locus to be haplotyped, and can therefore be time-consuming and expensive. Such differential priming methods do not rely on the use of probes.

Figure 1:
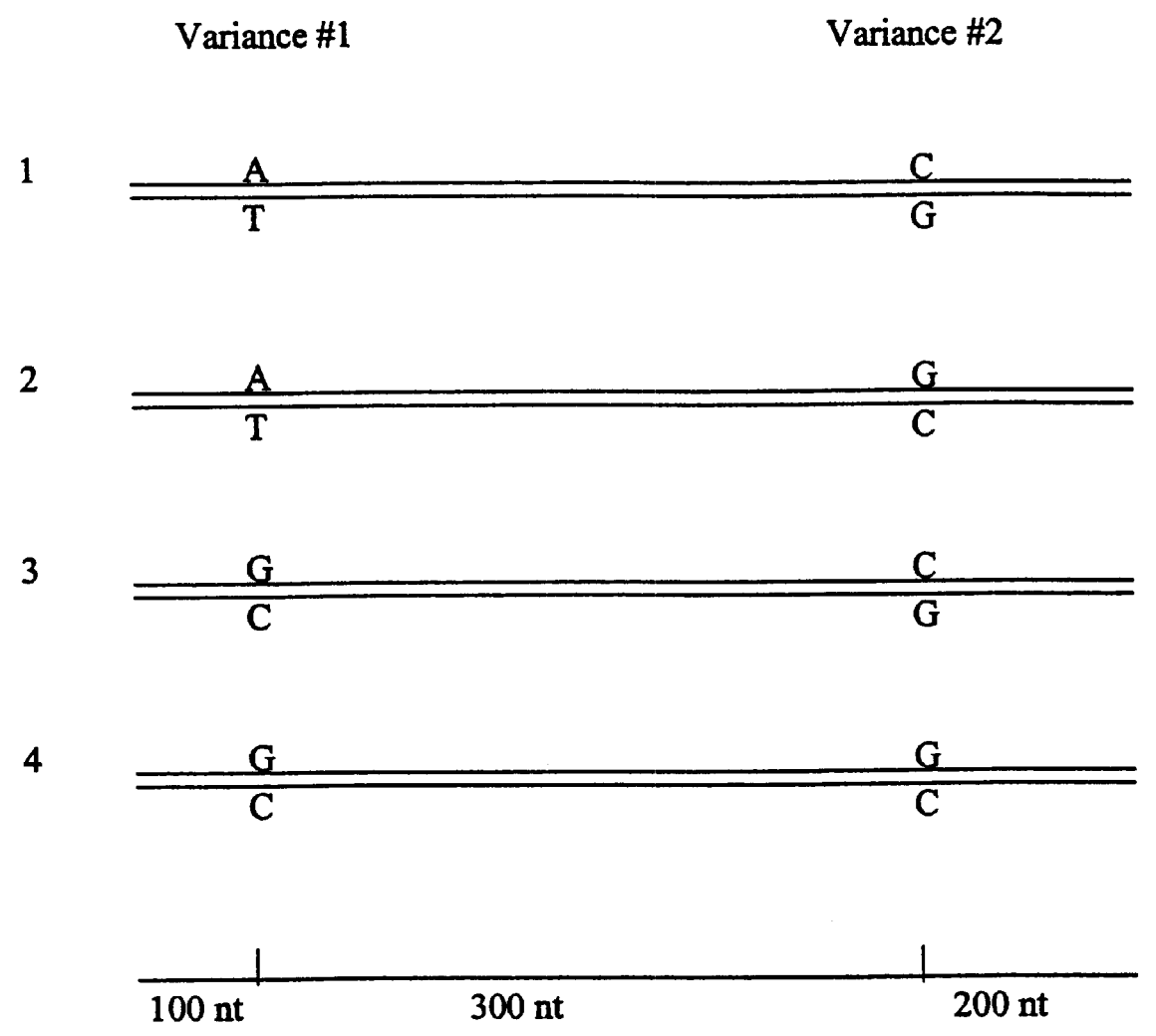

The production of hemizygous probes from hemizygous cells as described herein is useful for the determination of haplotypes, using a procedure based on formation and detection of heteroduplexes between probe and sample strands. As shown in the example schematically diagramed in FIG. 1, two variances 300 nucleotides (nts) apart can be amplified together on a 600 nucleotide (nt) PCR product. There are four possible alleles (numbered 1–4 to the left of FIG. 1), comprising all the possible pair-wise combinations of variances. For example, for individuals heterozygous at both variance #1 and variance #2, there are only two types of heterozygotes in whom this will occur: heterozygotes for alleles 1+4 or for alleles 2+3. The other four possible combinations of different alleles, 1+2, 1+3, 2+4 and 3+4, are only heterozygous at one position. Thus, there is no problem determining haplotypes; a genotyping procedure is sufficient. (Note that if each of the four alleles is duplicated, there are also four classes of homozygotes.)

Hemizygous probes derived from each of the four alleles may be used to type the possible classes of allele pairs. Table II below shows the cleavage fragments that would be generated by a resolvase, such as T4 endonuclease 7, or by chemical cleavage, after formation of heteroduplexes between samples, with the genotypes (allele pairs shown across the top and the labelled probes shown (by allele number) in the left column.

TABLE II

Cleavage Products of FIG. 1

| | Genotype of the sample | | | | | | | | | |
|---|---|---|---|---|---|---|---|---|---|---|
| | Double heterozygotes | | Single heterozygotes | | | | Homozygotes | | | |
| Probe allele | 1 + 4 | 2 + 3 | 1 + 2 | 1 + 3 | 2 + 4 | 3 + 4 | 1 + 1 | 2 + 2 | 3 + 3 | 4 + 4 |
| 1 | | 500 | | 500 | | 500 | | | 2 × 500 | |
| | | 400 | 400 | | 400 | | | 2 × 400 | | |
| | 300 | | | | 300 | 300 | | | | 2 × 300 |
| | 200 | 200 | 200 | 2 × 200 | | 200 | | 2 × 200 | | 2 × 200 |
| | 100 | 100 | | 100 | 100 | 2 × 100 | | | 2 × 100 | 2 × 100 |
| 2 | 500 | | | | 500 | 500 | | | | 2 × 500 |
| | 400 | | 400 | 400 | | | 2 × 400 | | | |
| | | 300 | | | 300 | 300 | | | 2 × 300 | |
| | 200 | 200 | 200 | 2 × 200 | | 200 | 2 × 200 | | 2 × 200 | |
| | 100 | 100 | | 100 | 100 | 2 × 100 | | | 2 × 100 | 2 × 100 |
| 3 | 500 | | 500 | 500 | | | 2 × 500 | | | |
| | 400 | | | | 400 | 400 | | | | 2 × 400 |
| | | 300 | 300 | | 300 | | | 2 × 300 | | |
| | 200 | 200 | 200 | 2 × 200 | | 200 | | 2 × 200 | | 2 × 200 |
| | 100 | 100 | 2 × 100 | 100 | 100 | | 2 × 100 | 2 × 100 | | |
| 4 | | 500 | 500 | | 500 | | | 2 × 500 | | |
| | | 400 | | 400 | | 400 | | | 2 × 400 | |
| | 300 | | 300 | 300 | | | 2 × 300 | | | |
| | 200 | 200 | 200 | 2 × 200 | | 200 | 2 × 200 | 2 × 200 | | |
| | 100 | 100 | 2 × 100 | 100 | 100 | | 2 × 100 | 2 × 100 | | |

Table II shows a model that assumes, for ease of presentation, complete cutting at sites of base mispairing. Use of this assay, however, does not rely upon complete cutting since there is a predictable relationship between the presence of mispaired bases (cleavage sites) and the ratio of products produced that will generally allow data such as that shown in Table II to be inferred from actual data.

For example, in the combination of probe #1 with heterozygous sample 1+4, Table II shows cleavage products of 300 nt, 200 nt, and 100 nt. There might also be incompletely cleaved products of 300+200=500 and 300+100=400. However, comparison of the intensity of the 400 nt cleavage products between probe #1/sample 1+4 and probe #1/sample 1+2, or the 500 nt cleavage products between probe #1/sample 1+4 and probe #1/sample 1+3, would reveal a relative loss of intensity of those [400 nt and 500 nt] products in the probe #1/sample 1+4 heteroduplex cleavage product due to cleavage at an intervening site. (Note that Table II does not show uncleaved products.)

Table II indicates, first, that if heteroduplexes can be detected quantitatively (i.e., if two copies of a 100 nt product can be distinguished from one copy), all 10 genotypes can be distinguished by a single hemizygous probe. The possibility exists, however, in many heteroduplex-based variance detection procedures using, for example, T4 endonuclease VII, of some variation in cleavage efficiencies which may affect quantitative analysis of the data.

The second conclusion that can be drawn from Table II is that, even without precise quantitation, the two haplotypes in the double heterozygote samples (1+4 and 2+3 on Table II) can be distinguished qualitatively. Hence, data generated using this assay can be analyzed both quantitatively as well as qualitatively. For example, if a genotyping procedure were done on all samples first to determine which individuals were double heterozygotes (and therefore needed to be haplotyped), then a subsequent heteroduplex-based haplotype assay using a hemizygous probe would give unambiguous haplotype results. This two step approach (genotyping first, then haplotyping) is a practical, albeit time-consuming, solution to haplotyping.

The third conclusion that can be drawn from Table II is that the cleavage product pattern from homozygotes mimics the cleavage product pattern observed in some of the heterozygote samples (for example, a probe produced from allele #1 gives the same size products with both heterozygous 1+4 and homozygous 4+4 in Table II). Such a result may lead to confusion in determining the haplotype of a sample.

To effectively deal with this situation, the present approach may be carried out with more than one hemizygous probe used in a serial fashion. The aggregate data from multiple probe-sample heteroduplexes greatly facilitates the identification of haplotypes by providing both complementary and redundant data. It is straightforward to determine all haplotypes (even in the absence of genotype data) from, for example, resolvase cleavage patterns. Table II illustrates the complementary patterns of cleavage expected with the use of different hemizygous probes (probes #1–#4). A clear example of the utility of using multiple probes is the instance in which a series of probes have progressively more mispaired bases with the test alleles. The progressive appearance of smaller products (adding up to the size of larger products detected with other probes with fewer mispairs) is an indication that the same allele is being progressively cut, and therefore that all the variances from the hemizygous probe lie on that allele. For example, the presence of a series of heteroduplex cleavage patterns with different probes showing weakening or disappearance of a 350 nt product with appearance of 200 nt+150 nt products, and weakening or disappearance of the 200 nt product with appearance of 120 nt+80 nt products would indicate the mispaired bases responsible for the cleavage of the 350 nt and 200 nt fragments lie on the same allele.

For the purposes of determining haplotypes, two or more hemizygous probes are preferably used in separate experiments on a set of samples to produce and analyze heteroduplexes. In addition, any number of probes, for example, three, or, more preferably, four or more probes, may be utilized for heteroduplex analysis. Note that, although there are only four possible alleles in the case illustrated in FIG. 1 and Table II, a fragment with three variances would have $2^3$, or 8 possible haplotypes, and a fragment with four variances would have $2^4$, or 16 possible haplotypes, and so on. All possible haplotypes, however, are rarely observed. Hence, the ability to generate numerous hemizygous probes from multiple hemizygous cells using the methods described herein represents an ideal way to produce the multiple probes necessary to determine genotypes from analysis of heteroduplex products.

All publications and patent applications mentioned in this specification are herein incorporated by reference to the same extent as if each independent publication or patent application was specifically and individually indicated to be incorporated by reference.

Other embodiments are within the claims.

What is claimed is:

1. A method for analyzing a test nucleic acid sample to determine whether it contains a sequence variance, said method comprising the steps of:

(a) obtaining a nucleic acid probe from a hemizygous cell, wherein substantially all of the chromosomes in said cell are derived from a single parental copy, and said probe is complementary to a hemizygous chromosome or segment thereof present in said hemizygous cell;

(b) providing a test nucleic acid sample, wherein either said test nucleic acid sample is unlabeled and said probe is labeled or said test nucleic acid sample is labeled and said probe is unlabeled;

(c) forming a duplex between said test nucleic acid sample and said probe; and (d) analyzing whether said duplex contains a nucleotide mismatch, thereby determining whether said test nucleic acid sample contains a sequence variance.

2. The method of claim 1, wherein said determining step is carried out using a denaturing gradient gel electrophoresis technique.

3. The method of claim 1, wherein said nucleotide mismatch represents a sequence variance in a population.

4. The method of claim 1, wherein said probe has a known sequence.

5. The method of claim 1, wherein said probe is detectably labeled.

6. The method of claim 1, wherein said hemizygous cell results from the loss of a chromosome or segment thereof.

7. The method of claim 1, wherein said hemizygous cell comprises multiple copies of said hemizygous chromosome or segment thereof.

8. The method of claim 1, wherein said hemizygous cell is human.

9. The method of claim 1, wherein said hemizygous cell is an immortalized cell.

10. The method of claim 1, wherein said hemizygous cell is derived from a complete hydatidiform mole, an ovarian teratoma, an acute lymphocytic leukemia, an acute myeloid leukemia, a solid tumor, a squamous cell lung cancer, an endometrial ovarian cancer, a malignant fibrous histiocytoma, or a renal oncocytoma.

11. The method of claim 1, wherein said hemizygous cell is NALM-16 or KBM-7.

12. The method of claim 1, wherein said hemizygous cell is derived from a haploid germ cell.

13. The method of claim 1, wherein the presence of said nucleotide mismatch correlates with a level of therapeutic responsiveness to a drug or other therapeutic intervention.

14. The method of claim 1, wherein the presence of said nucleotide mismatch indicates a disease or condition, or a predisposition to develop said disease or condition.

15. The method of claim 1, wherein said nucleic acid probe is produced by amplifying at least a portion of said hemizygous chromosome or segment thereof to produce said probe.

16. The method of claim 1, wherein said determining step utilizes a protein that binds or cleaves said nucleotide mismatch.

17. The method of claim 16, wherein said protein is MutS.

18. The method of claim 16, wherein said protein is a resolvase.

19. The method of claim 18, wherein said resolvase is T4 endonuclease VII.

20. The method of claim 1, wherein said determining step utilizes a chemical agent that detects said nucleotide mismatch.

21. The method of claim 1, wherein said method is used to determine the haplotype of said nucleic acid sample.

22. The method of claim 10, wherein said hemizygous cell is an immortalized cell derived from a complete hydatidiform mole, an ovarian teratoma, an acute lymphocytic leukemia, an acute myeloid leukemia, a solid tumor, a squamous cell lung cancer, an endometrial ovarian cancer, a malignant fibrous histiocytoma, or a renal oncocytoma.

23. A method for analyzing a test nucleic acid sample to determine whether it contains a sequence variance, said method comprising the steps of:
  (a) obtaining a nucleic acid probe standard from a hemizygous cell, wherein substantially all of the chromosomes in said cell are derived from a single parental copy, and said probe is complementary to a hemizygous chromosome or segment thereof present in said hemizygous cell;
  (b) providing a test nucleic acid sample;
  (e) subjecting said probe standard and said test nucleic acid sample to non-denaturing gel electrophoresis; and
  (f) analyzing whether said test nucleic acid sample has a different electrophoretic mobility than said probe standard, thereby determining whether said test nucleic acid sample contains a sequence variance.

24. The method of claim 23, further comprising performing the following steps prior to said electrophoresis:
  (a) subjecting said probe standard and said test nucleic acid sample to denaturation conditions; and
  (b) subjecting said denatured probe standard and said denatured test nucleic acid sample to reannealing conditions that allow said probe standard and said test nucleic acid sample to adopt a single-stranded conformation.

25. The method of claim 23, wherein said probe standard and said test nucleic acid sample are present in a double-stranded conformation.

26. The method of claim 23, wherein said test nucleic acid sample is cleaved using a protein prior to said electrophoresis.

27. The method of claim 23, wherein said sequence variance represents a sequence variance in a population.

28. The method of claim 23, wherein said probe has a known sequence.

29. The method of claim 23, wherein said probe is detectably labeled.

30. The method of claim 23, wherein said hemizygous cell comprises multiple copies of said hemizygous chromosome or segment thereof.

31. The method of claim 23, wherein said hemizygous cell is human.

32. The method of claim 23, wherein said hemizygous cell is an immortalized cell.

33. The method of claim 23, wherein said hemizygous cell is derived from a complete hydatidiform mole, an ovarian teratoma, an acute lymphocytic leukemia, an acute myeloid leukemia, a solid tumor, a squamous cell lung cancer, an endometrial ovarian cancer, a malignant fibrous histiocytoma, or a renal oncocytoma.

34. The method of claim 33, wherein said hemizygous cell is an immortalized cell derived from a complete hydatidiform mole, an ovarian teratoma, an acute lymphocytic leukemia, an acute myeloid leukemia, a solid tumor, a squamous cell lung cancer, an endometrial ovarian cancer, a malignant fibrous histiocytoma, or a renal oncocytoma.

35. The method of claim 23, wherein said hemizygous cell is NALM-16 or KBM-7.

36. The method of claim 23, wherein said hemizygous cell is derived from a haploid germ cell.

37. The method of claim 23, wherein the presence of said sequence variance correlates with a level of therapeutic responsiveness to a drug or other therapeutic intervention.

38. The method of claim 23, wherein the presence of said sequence variance indicates a disease or condition, or a predisposition to develop said disease or condition.

39. The method of claim 23, wherein said nucleic acid probe is produced by amplifying at least a portion of said hemizygous chromosome or segment thereof to produce said probe.

\* \* \* \* \*